US006888779B2

(12) United States Patent
Mollicone et al.

(10) Patent No.: US 6,888,779 B2
(45) Date of Patent: May 3, 2005

(54) METHOD AND APPARATUS FOR A WAKING CONTROL SYSTEM

(75) Inventors: Daniel Joseph Mollicone, Vancouver (CA); Matthew Vit van Wollen, Vancouver (CA)

(73) Assignee: Pulsar Informatics, Inc., Vancouver (CA)

(*) Notice: Subject to any disclaimer, the term of this patent is extended or adjusted under 35 U.S.C. 154(b) by 370 days.

(21) Appl. No.: 09/991,353

(22) Filed: Nov. 20, 2001

(65) Prior Publication Data

US 2003/0095476 A1 May 22, 2003

(51) Int. Cl.$^7$ .................. G04B 47/00; G04B 23/02; G04C 21/00; A61M 21/00; A61B 5/24
(52) U.S. Cl. .................. 368/10; 368/73; 368/245; 368/250; 600/500; 600/529; 600/544
(58) Field of Search ................. 600/500, 529, 600/544; 368/10–12, 72–74, 244, 245, 250

(56) References Cited

U.S. PATENT DOCUMENTS

| | | | | |
|---|---|---|---|---|
| 4,228,806 A | * | 10/1980 | Lidow | 600/544 |
| 4,234,944 A | * | 11/1980 | Komaki et al. | 368/72 |
| 5,101,831 A | * | 4/1992 | Koyama et al. | 600/500 |
| 5,197,941 A | * | 3/1993 | Whitaker | 600/27 |
| 5,846,206 A | * | 12/1998 | Bader | 600/534 |
| 5,928,133 A | * | 7/1999 | Halyak | 600/26 |
| 6,236,622 B1 | * | 5/2001 | Blackman | 368/10 |

* cited by examiner

Primary Examiner—Vit W. Miska
(74) Attorney, Agent, or Firm—Oyen Wiggs Green & Mutala (57) ABSTRACT

A method and apparatus are disclosed for a waking system that wakes an individual gradually over a period of time in order to promote the wellness of that individual. The user sets the system controller with a desired final wakeup time, which is the time that the user must be awake. When the actual time reaches a stimulus introduction time (i.e. some time prior to the desired final wakeup time), the system controller causes the introduction of stimulus. The system further comprises a detection system that measures a parameter correlated to the individual's sleep level (preferably motion). This measured parameter is then used in a feedback loop to control the level of stimulus experienced by the individual. In this manner, the user is woken gradually over a period of time between the stimulus introduction time and the desired final wakeup time, without introducing any sudden shocks to the user's physiological systems.

41 Claims, 6 Drawing Sheets

METHOD AND APPARATUS FOR A WAKING CONTROL SYSTEM

FIELD OF THE INVENTION

The invention described herein relates to waking devices. Specifically, the invention relates to waking devices that gradually increase stimulus to individuals so as to wake them gradually in a manner that promotes wellness.

BACKGROUND OF THE INVENTION

The most common waking device is the "alarm" clock. Conventional alarm clocks wake individuals by creating abrupt and sudden changes in sound, light or other stimuli, so as to shock or alarm the user, ending the sleeping process. It has long been thought that such a rapid manner of waking does not promote wellness, because of the shock induced into the user's physiology by the abrupt introduction of stimuli.

Arrange of prior art has been developed to help minimize the shock introduced by conventional alarm based waking systems. One common method of reducing the shock to individuals' physiological systems is to trigger the alarm stimulus in a conventional manner and then allow the alarm stimulus to be interrupted by the user for one or more brief periods. This method of interrupting the alarm stimulus is commonly referred to as a "snooze" feature and is conventionally implemented using a button on the alarm clock. Several more sophisticated waking systems use methods other than buttons to activate the "snooze" feature.

Such waking systems include those of: (i) U.S. Pat. No. 4,670,864, which incorporates an audio or voice activated snooze function; (ii) U.S. Pat. No. 4,894,813, which discloses an ultrasonic or infrared motion detector to activate the snooze function; and (iii) U.S. Pat. No. 5,524,101, which discloses a motion detector to activate the snooze function.

The snooze function helps to reduce the shock to a user's physiology by allowing the user to wake over an extended period of time. The principal drawback with all of the waking devices that incorporate the snooze method is that they still involve the introduction of a constant and preset intensity of alarm stimulus, which changes almost instantaneously from an ambient level to an alarm intensity stimulus level in the manner of a step function. For example, an alarm clock may be set such that the alarm stimulus (i.e. a buzzer) is of a constant and predetermined volume. When the waking device is triggered at the wakeup time, the buzzer is instantaneously activated at this predetermined volume level until the user activates the snooze function. Since the individual user must actually be awake to activate the snooze feature, the predetermined stimulus level must still shock the user's physiological systems to some degree in order to actually wake them.

Another method of reducing the shock to a user's physiological systems introduced by a waking device is to gradually increase the stimulus level experienced by the user over a period of time. This technique represents a considerable improvement over both conventional alarm type waking devices and those incorporating the "snooze method", because the stimulus is introduced gradually (as opposed to as a step function). A gradual introduction of stimulus does not shock the system to the same degree as a stimulus introduced via a step function.

U.S. Pat. No. 4,038,561 discloses a light source and a tape deck that include a timer mechanism that gradually increases or decreases the light intensity and the volume of the tape deck. The ultimate stimulus intensity (i.e. the highest level of light and volume intensity) and the rate or profile of increase or decrease of the stimulus is preset in accordance with user or system determined conditions. The tape deck and the light source can also be operated independently from one another (i.e. both the light source and the tape deck may be preset with different ultimate intensities, different rates of stimulus increase or decrease and different stimulus introduction times).

U.S. Pat. No. 4,234,944 discloses an alarm timing device that gradually increases the volume of audio stimulus over a period prior to the desired final wakeup time. Prior to going to sleep each night, the user sets the desired final wake up time (i.e. 7:00 AM) and the stimulus introduction time (i.e. 10 minutes before the desired final wakeup time). With these settings, the system introduces an audio stimulus at a low level at 6:50 AM and then the increases the volume of the stimulus gradually until the waking time of 7:00 AM. The system therefore wakes the user at some time between the stimulus introduction time and the desired final wakeup time, when the volume of the audio stimulus is sufficiently high for the user to cross their personal threshold between being asleep and being awake.

U.S. Pat. No. 5,212,672 teaches a timing control apparatus for selectively activating at least one remote stimulus device, such as a light source, an audio source and an aroma generator and increasing the intensity level of the remote stimulus device(s) from zero to full intensity over a period of time. In this manner the timing device allows the user to be awoken at some time between the stimulus introduction time and the desired final wakeup time, when the intensity of the stimulus is sufficiently high for the user to cross their personal threshold between being asleep and being awake. The invention relies on the generation of electronic pulses, which are introduced to the system at the stimulus introduction time and then counted, so as to increase the intensity of the stimulus devices in a substantially linear manner with the pulse count. As with some of the above described inventions, the user presets the desired final wakeup time and either the system or the user can set the stimulus introduction time.

U.S. Pat. No. 6,236,622 describes a lighting fixture with a lamp and an alarm clock that may operate in a wake-up cycle or a sleep cycle. The user may independently set the stimulus introduction time of the light source and the audio source in the wake-up cycle, so that the stimulus starts at the stimulus introduction time and gradually increases over time to a preset finish time. The rate of increase for both the light source and the audio source can be independently controlled by the user by varying the stimulus introduction time and the finish time. The invention also has a sleep cycle, wherein the stimulus may be gradually decreased over time. As with the above-described inventions, the stimulus introduction time and the rate of change in the intensity of the stimulus are preset by the user.

The principal disadvantage of the inventions described by U.S. Pat. Nos. 4,038,561, 7,234,944, 5,212,672 and 6,236,622 is that the rate and/or profile of the stimulus increase is either preset by the user or predetermined by the waking system. These techniques incorporate no feedback and are not responsive to a variable personal waking threshold, which for a given individual changes over time and is also dependant on a number of other factors. Factors that may influence an individual's personal waking thresholds include: (i) the variance in intensity that may wake different types of sleepers (i.e. light sleepers as compared to heavy sleepers); (ii) the stage of sleep that the user is in when the stimulus is introduced (i.e. stage 1, 2, 3, 4 or Rapid Eye Movement (REM)); (iii) the time that the user went to sleep (i.e. total amount of sleep that night); (iv) the phase of the user's "circadian rhythms"; (v) the amount of sleep that the user has had in the last number ofl days; (vi) the ambient stimulus level in the sleeping environment (i.e. if there is more ambient stimulus, then it will take a higher stimulus level to wake the user); and (vii) the amount of sunlight at that time of year (i.e. in the winter months, when there is less sunlight, an individual typically has higher waking thresholds). The gradual stimulus increase taught by the prior art does not necessarily match the optimal set of waking conditions for an individuals particular waking threshold at a given waking time. U.S. Pat. No. 5,928,133 (referred to herein as the '133 patent) attempts to monitor a user's sleep pattern to determine the "optimum time" to wake them. The invention incorporates a sensor comprising a pair of electrodes to measure the resistance of the user's body and to determine therefrom the user's delta waves. When individuals go through the various phases of sleep, they emit delta waves that vary in a predictable manner. At the beginning and end of each REM cycle, these delta waves exhibit spikes, where the user comes close to their waking threshold. The '133 patent allows the user to set the interval during which they want to be awoken. When the actual time reaches this predetermined waking interval, the system responds to a spike in the user's delta waves and then triggers a conventional alarm that wakes the user at that time. One drawback with the 133 patent is that it teaches a conventional alarm, having a constant stimulus level to wake the user. Even though the alarm is triggered at the "optimum time" (i.e. during spikes in the delta waves), the waking threshold for each user varies as mentioned previously, and the constant level of stimulus output may be excessive or in the alternative insufficient for a given waking threshold. Also, the level of delta wave activity during delta wave spikes is different for each such spike. Consequently, in circumstances where there is a relatively low spike in the user's delta waves and the user has a relatively high waking threshold, the user is still woken in a manner that introduces shock to their physiological systems. Another drawback of the '133 patent is that the user must define a range of acceptable waking times, and may be woken at any time within that range. However, it is advantageous to be woken substantially close to the final (desired) waking time, so as to maximize sleep. Yet Another drawback with the '133 patent is that it requires physical contact with the user (i.e. electrodes) in order to measure the user's delta waves. Although the '133 patent discloses the potential for wireless communication between the electrodes and the timing device, the electrodes themselves must still be in contact with the user, which may cause the discomfort to the user and may inhibit the ability of the user to sleep.

SUMMARY OF THE INVENTION

The present invention discloses an apparatus for waking an individual in a manner that promotes their well being. The apparatus comprises: (a) a detection system that measures at least one parameter correlated to the individual's sleep level; and (b) a controller, which controls the introduction of stimulus at a stimulus introduction time and, using the measured parameter as an input, controls the stimulus intensity experienced by the individual. In this manner, the apparatus is able to wake the individual gradually over a period of time between the stimulus introduction time and a final wakeup time, preferably substantially close to the final wakeup time.

The intensity of each stimulus may be independently controlled.

The parameter measured by the detection system may be motion of the individual and the detection system may comprise either an ultrasonic motion detector or an infrared motion detector.

The parameter measured by the detection system may be one or more of, motion, brain waves, skin potential, skin resistance, muscle tone, eye movement, heart rate and breathing rate of the individual.

The apparatus may further comprise a user interface with an input mechanism (for receiving input from the individual) and an output mechanism (for communicating information to the individual).

The input mechanism may be any one or more of: a voice recognition system, a keypad, a touch screen interface, a remote control device and a plurality of buttons and switches. The output mechanism may be one or more of: a liquid crystal display, a light emitting diode display, an analog clock display, a plasma screen display, a cathode ray tube display, an audio output device and a plurality of switch and button indicators.

The types of information input by the user via the input mechanism and reflected to the user via the output mechanism may include: the final wakeup time, the particular set of stimuli desired, the relative intensity of each stimulus selected, the stimulus introduction time, the actual time, the date, a status as to whether the apparatus is armed or unarmed, the individual's personal sleep sensitivity level, the individual's recent sleep history, an ambient stimulus level in the individual's sleeping environment and a seasonal amount of daylight.

The introduced stimulus may be one or more of; a heat stimulus, a light stimulus, a sound stimulus, an olfactory stimulus and a tactile stimulus.

Another aspect of the present invention involves a method of waking an individual in a manner that promotes the individual's well being. The method comprises several steps including: (a) setting the system with a desired final wakeup time; (b) measuring at least one parameter correlated to the individual's sleep level; (c) introducing stimulus to the individual's sleeping environment at a stimulus introduction time; and (d) using the measured parameter to control the introduced stimulus intensity, so as to wake the individual gradually over a period of time between the stimulus introduction time and the final wakeup time, preferably substantially close to the final wakeup time.

As a part of the process of controlling the stimulus intensity experienced by the individual, the parameter measured by the detection system may be input to the controller at least once, or continuously at a particular high frequency. A feedback loop may be used.

Further advantages of the invention will become apparent when considering the drawings in conjunction with the detailed description.

DESCRIPTION OF THE PREFERRED EMBODIMENT

Figure 1:
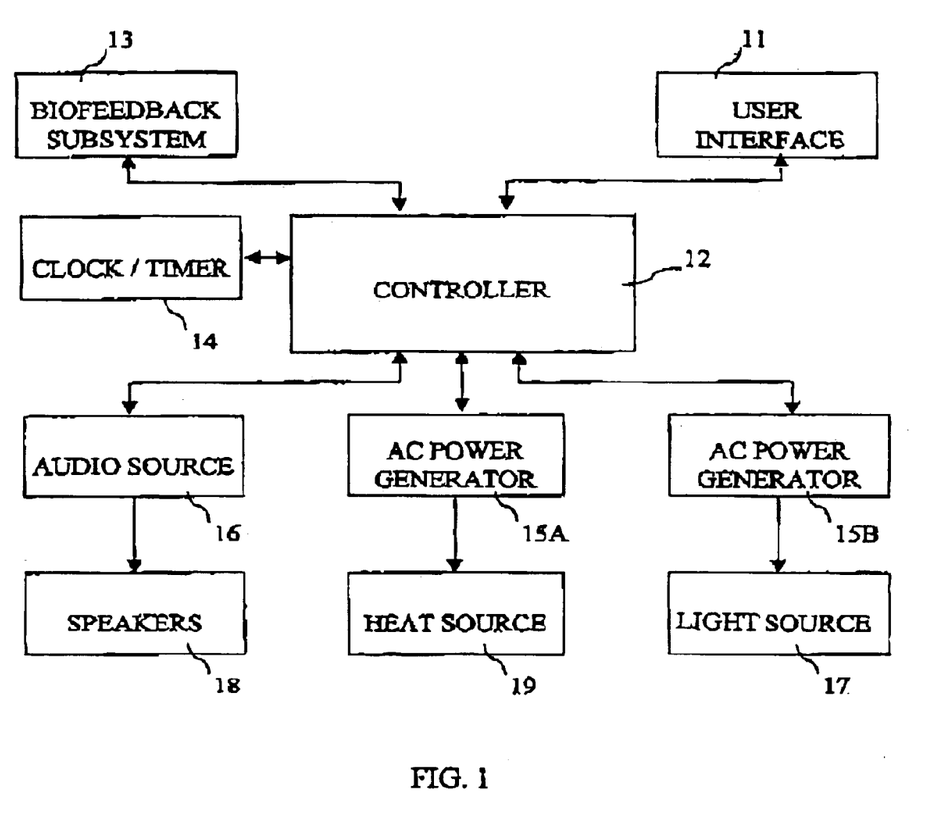
FIG. 1 represents a overview of the principal components of the waking method and apparatus disclosed in the present invention.

Referring to FIG. 1, a system architecture is depicted for the waking system 10 in accordance with the present invention. The waking system 10 is made up of a number of distinct subsystems and components, each of which interacts with the controller 12. The controller 12 directs the interaction of the various subsystems and components with one another and is ultimately responsible for the operation of the waking system 10. In a preferred embodiment, the controller 12 is a microprocessor, such as the PIC 16C745, which can be used in an embedded system environment. However, the invention is not dependent on the type of controller 12 that is used. Other suitable controllers include: other microprocessor chips, integrated circuit controllers, printed circuit board controllers and even computers. In general, the controller 12 should be understood to include any device capable of accessing and executing instructions stored in memory and capable of interacting with its external environment to receive input and provide output.

Controller 12 is linked to a system clock 14. Preferably, the system clock 14 comprises an oscillating crystal or other time keeping means that is easily incorporated into an embedded system circuit. However, the invention does rot depend on the manner in which the system clock 14 operates. Other sources of timing information and variations of the system clock 14 include: radio receivers operative to receive broadcast time data, microprocessor firmware clocks (i.e. which may be internal to the controller 12), integrated circuit clocks and mechanical clocks. When a user (not shown in FIG. 1) sets the time and date via the user interface 11, the system clock 14 and the controller 12 work together to provide meaningful time and date output, which is displayed on the user clock 21 (see FIG. 2) as a part of the user interface 11. It should be noted that if the system clock 14 is of the type that receives broadcast time data, then there is no need for the user to set the time and date. In addition to working with the controller 12 to provide the user clock 21, the system clock 14 is also operative to trigger subroutines in the controller 12.

Figure 2:
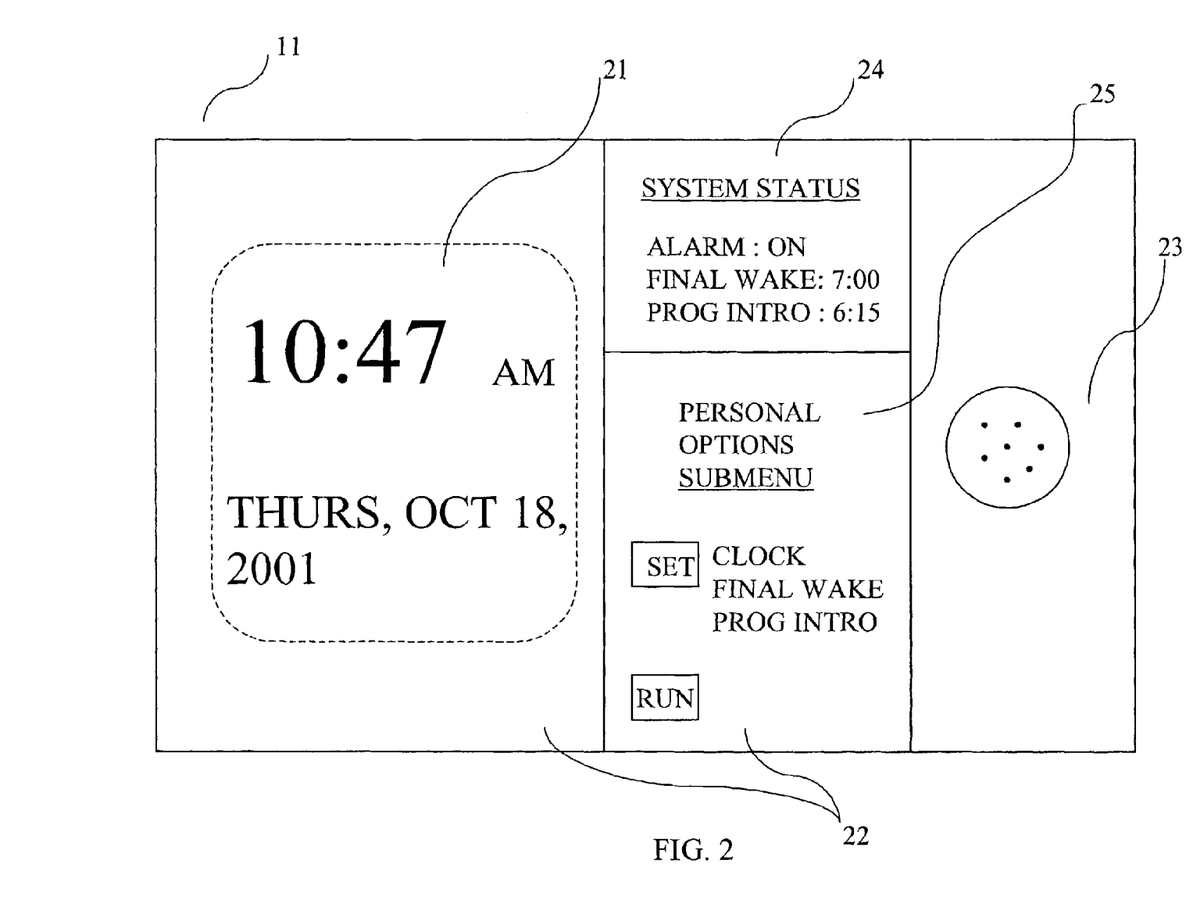
FIG. 2 displays a representative embodiment of the user interface for the waking system.

One possible embodiment of the user interface 11 is depicted in FIG. 2. In general, the user interface 11 contains an input mechanism 23, through which the user provides instructions to the waking system 10, and an output mechanism 22, through which the user tells the time date and receives information about the system status and any personal options. In the preferred embodiment of the user interface 11, the user provides input information and instructions to the waking system 10 via a voice recognition input system 23 (depicted as a microphone input in FIG. 2.) Voice recognition input systems typically include voice recognition chip hardware, voice recognition software, and other electronic components. The status of the input information and instructions is reflected back to the user on a liquid crystal display (LCD) output mechanism 22. Both voice recognition systems and liquid crystal displays are well known in their respective fields.

As mentioned above, user input information includes the actual time and date (which are reflected on the user clock 21), except in cases where the system clock 14 is operative to receive broadcast time data. Other input information may include: (i) an alarm on/off switch; (ii) a desired final waking time (i.e. the time that the user must be awake); and (iii) a stimulus introduction time (i.e. the point in time, prior to the final waking time, at which the introduction of stimulus starts). FIG. 2 shows examples of user input information as displayed by the LCD output mechanism 22, with the user clock 21 reading 10:47 AM on Thursday Oct. 18, 2001, the alarm switch toggled to the ON position, the final wakeup time being 7:00 AM and the stimulus introduction time being 6:15 AM. The user clock 21 on the user interface 11 may have a digital or analog display that enables the user to tell the time.

In addition to the above-mentioned information, the user may also be able to input other types of information that will help personalize the operation of the waking system 10. Such additional user input information is optional and may include: (i) a time that the user went to bed; (ii) a personal waking threshold level (i.e. whether the user is a light or heavy sleeper, which may be reflected on a scale of 1–10); and (iii) recent sleep patterns over the last number of days. The system 10 and the user interface 11 may also make provisions for the user to enter other information, such as the total number of daylight hours (i.e. which may vary from season to season) and the ambient level of stimulus. Alternatively, the system may automatically select these criteria based on its knowledge of the date (which allows it to calculate total sunlight time) and using the microphone part of its voice activated input mechanism 23 (which allows it to measure ambient sound level). These personal options and/or system calculated information may be displayed on the system status portion 24 of the output mechanism 22 or, alternatively, the personal options may be contained in a sub-screen or sub-menu 25 of the system status portion 24, as is the case in FIG. 2.

As mentioned above, the preferred embodiment of the user interface 11 is a liquid crystal display output mechanism 22 with a voice actuated input mechanism 23. However, there are many other methods and devices that may form suitable user interfaces. Other types of input mechanisms include: 4×4 hex keypads (similar to those used on a telephone), special function buttons or switches, touch screen interfaces and remote control devices. Other types of output devices include: light emitting diode (LED) displays, analogue clock displays, plasma screen displays, cathode ray tube (CRT) displays, audio output devices, and simple switch indicators. In general, the technique and equipment used to implement the user interface 11 is not a critical aspect of the invention. However, an effective user interface 11 will be able to receive the required user input information and display the current time, date and system status in a manner that is easily interpreted by the user.

Figure 3:
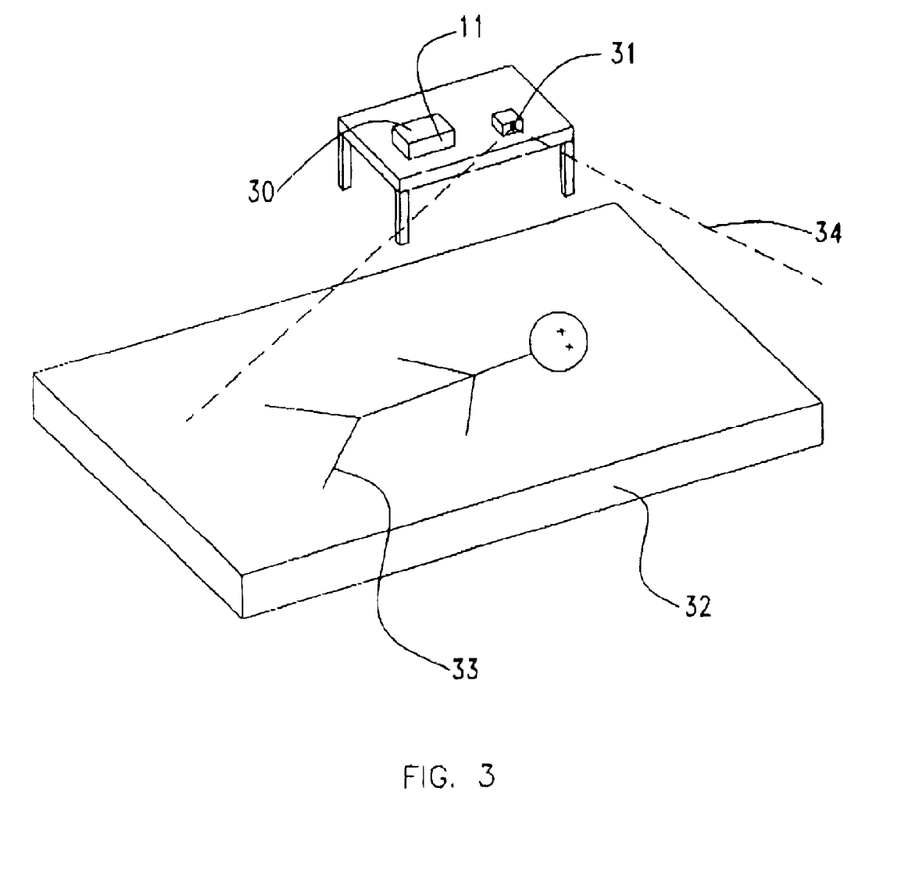
FIG. 3 depicts an embodiment of the biofeedback subsystem employing ultrasonic sensors disposed close to a sleeping user.

The biofeedback subsystem 13 measures the user's current state of sleep and feeds this information back to the controller 12. Using this feedback, the controller 12 manipulates the stimulus conditions to control the rate at which the user is waking and to bring the user gradually to a fully woken state at a time substantially close to the desired final wakeup time and without shocking the user's physiological systems. Referring to FIG. 3, the preferred embodiment of the biofeedback subsystem 13 comprises a motion detector 31. Typical motion detectors include: (i) ultrasonic sensors that sense movement though changes in pressure waves or mechanical waves; and (ii) infrared sensors that sense movement though changes in temperature profile and electromagnetic radiation. The movement level of human beings is correlated to their state of arousal and tends to increase as they move through various levels of sleep towards the waking state; consequently, ultrasonic and infrared movement sensors provide a good method of determining the user's state or level of sleep.

FIG. 3 depicts the waking system using an ultrasonic motion sensor 31. In general, the motion sensor 31 may be incorporated into the system housing 30 or may constitute one or more separate components, which communicate to the system via wired or wireless communication means. In some embodiments, it may be favorable to have the motion sensor 31 as a distinct element, because the sensor 31 can be positioned for more accurate movement detection and the system housing 30 can be positioned so that the user 33 can more easily read the user interface 11. The ultrasonic motion sensor 31 casts ultrasonic waves 34, which are reflected by the user 33 and the objects in their sleep environment 32, and returned to the sensor 31. When there is movement in the environment, the sensor detects differences in the reflected waves and is able to discern the movement. The ultrasonic waves emitted by the sensor 31 are not detectable by the user 33 and, as a result, such detectors are ideal because they do not impede the user's ability to sleep comfortably. It should be noted that FIG. 3 depicts the use of only one sensor 31, but generally it may be preferable to have multiple motion sensors and the invention should be understood to incorporate this concept.

Infrared motion sensors function in a manner similar to the ultrasonic sensor 31 depicted in FIG. 3; however, infrared motion detectors employ electromagnetic radiation rather than sonic waves.

Although the preferred embodiment of the invention depicted in FIG. 3 monitors the user's sleep level through a motion sensor 31, the invention may also use (and should be considered to incorporate) other techniques of measuring and determining the user's sleep level. Such sleep detection techniques include: (i) measurement of brain waves using electrical contacts on the user's head; (ii) measurement of the skin potential and/or resistance using electrical contacts on the user's skin; (iii) measurement of muscle tone through contact with the user's skin; (iv) measurement of eye movement using contacts located around the user's temples; (v) measurement of heart rate by electrical EKG contact to the user; (vi) measurement of user's pulse rate using a pressure transducer; and (vii) measurement of the user's breathing rate using an oxygen sensor, a carbon dioxide sensor or a pressure transducer located close to the user's abdomen.

The functionality of the biofeedback system 13 as it relates to the waking system 10 as a whole will be explained in more detail below.

Referring back to FIG. 1, the controller 12 also regulates the stimulus devices (i.e. the audio source 16, the heat source 19 and the light source 17). In the preferred embodiment, the stimulus devices can be divided into two groups: (i) the light 17 and heat 19 sources, which require AC power controllers 15A and 15B; and (ii) the audio source, which requires more intricate digital control techniques.

The invention can be used in conjunction with virtually any commercially available AC electrical heat source 19 and any commercially available AC electrical light source 17. External heat sources 19 and external light sources 17 plug directly into the AC power controllers 15A and 13B respectively, which are incorporated into the system housing (not shown in FIG. 1). Alternative embodiments of the invention may include the control system 10 packaged along with a suitable heat source 19 and/or a suitable light source 17.

Figure 4:
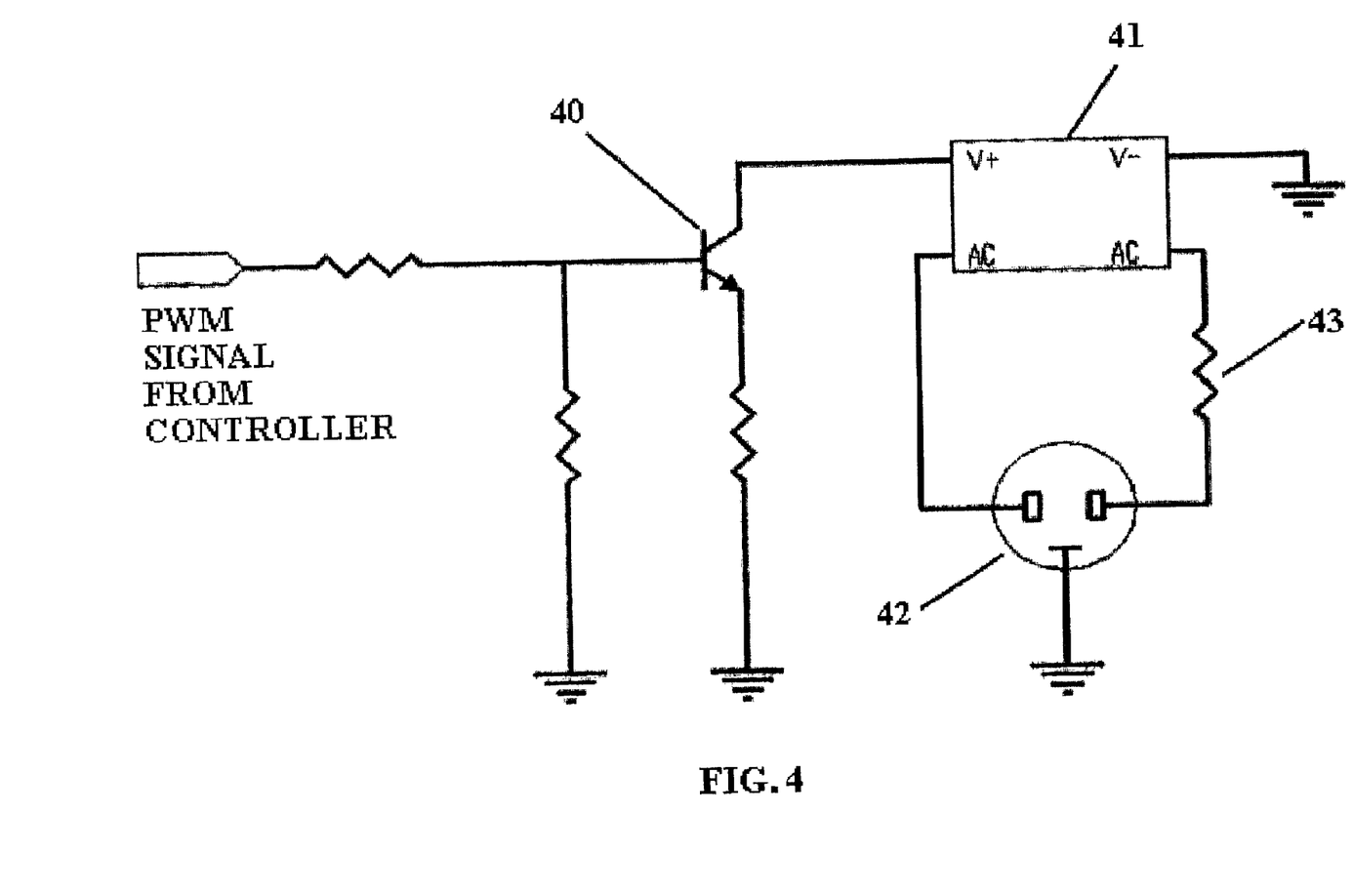
FIG. 4 depicts an example of a relay based AC power control circuit.

During operation when a certain stimulus level is desired, the controller 12 provides a control signal to each of the AC power controllers 15A and 15B, which in turn regulate the amount of AC power reaching the heat source 19 and the light source 17 respectively. In a preferred embodiment, the controller 12 emits pulse width modulated (PWM) control signals to the AC power controllers 15A and 15B and the duty cycle of the PWM signals determines the percentage of the AC power delivered to the heat source 19 and the light source 17. This type of AC power control may be easily achieved with the simple relay circuit depicted in FIG. 4. The PWM signal from the controller (not shown in FIG. 4) activates transistor 40, which in turn activates solid state relay 41. The switching action of solid state relay 41 toggles the AC power delivered to the socket 42 of the appropriate stimulus device (not shown), so that the stimulus device only receives an amount of AC power proportional to the duty cycle of the PWM signal. It should be noted here that the circuit of FIG. 4 is provided for demonstrative purposes and there are many methods of controlling AC power using the PWM or other control signals.

Such alternative methods include circuits using silicon controlled rectifiers (SCR's) or triacs. Although the preferred embodiment of the invention employs digitally controlled AC power, digitally controlled DC power may also be used. Moreover, the invention is independent of the technique used to effect this power control and should be understood to incorporate all such techniques.

It should also be noted here that other types of AC or DC controlled stimulus are envisaged as possible embodiments of the invention, including olfactory stimulus devices (i.e. aroma generators), tactile stimulus devices (i.e. wind, pressure, cold, vibration etc.), and humidity control devices. The invention should be understood to incorporate additional or alternative AC or DC controlled stimulus devices. It should be understood that the "stimulus" described in relation to the invention is an aggregate stimulus and may include a single stimulus or a plurality of stimuli, which may be independently controlled.

With regard to the audio source 16, the controller 12 is responsible for starting the audio source 16 and controlling its volume level. In general, the invention should be understood to incorporate any audio source 16 ranging from buzzer type noise makers to radio receivers, MP3 players, compact disk players, minidisk players, televisions and stereos. When using musical or vocal type audio sources 16 (i.e. stereos, MP3 players, tape players, compact disk players, radio tuners and televisions), it can be difficult to achieve the control of the stimulus intensity (i.e. volume) in the same manner used for the heat source 19 and the light source 17, because the switching of the AC power controller has a tendency to compromise the fidelity of the audio output, resulting in unpleasant sounding music or vocals. However, most music players and televisions produced today are digitally controlled, making them ideal for direct control by the system controller 12.

Referring back to FIG. 1, one embodiment of the invention includes the control system 10 packaged along with an audio source 16, which is preferably a CD player or an MP3 player. The controller 12 can control the audio source 16 by providing simple digital control signals via an industry standard RS232 connection or another type of digitally compliant connector. Mary CD players and MP3 players currently available, such as the Meridian 588, the Linn Sondek C12 and the Quadravox QV531 support digital control through an RS232 interface. It should be noted that the particular digital interface between the controller 12 and the audio source 16 is not a critical component of the invention and any such interface should be understood to be a part of the present invention.

Another embodiment of the invention involves a waking system 10 that incorporates a universal remote control (not shown in FIG. 1), which can be easily configured to control most commercially available audio sources 16. In such an embodiment, the waking control system 101 is packaged without the audio source 16, permitting the user to use their own audio source 16 in conjunction with the waking control system 10. The controller 12 is programmed so as to control an industry standard universal remote control using standard protocol.

Common industry standards for universal remote control devices include the Home Audio/Video interoperability (HAVi) standard (developed by Grundig, Hitahchi, Matsushita, Philips, Sony, Sharp, Thompson and Toshiba) and the nonproprietary Universal Remote Console Communication (URCC) protocol developed by the Infrared Data Association (IrDA).

Figure 5:
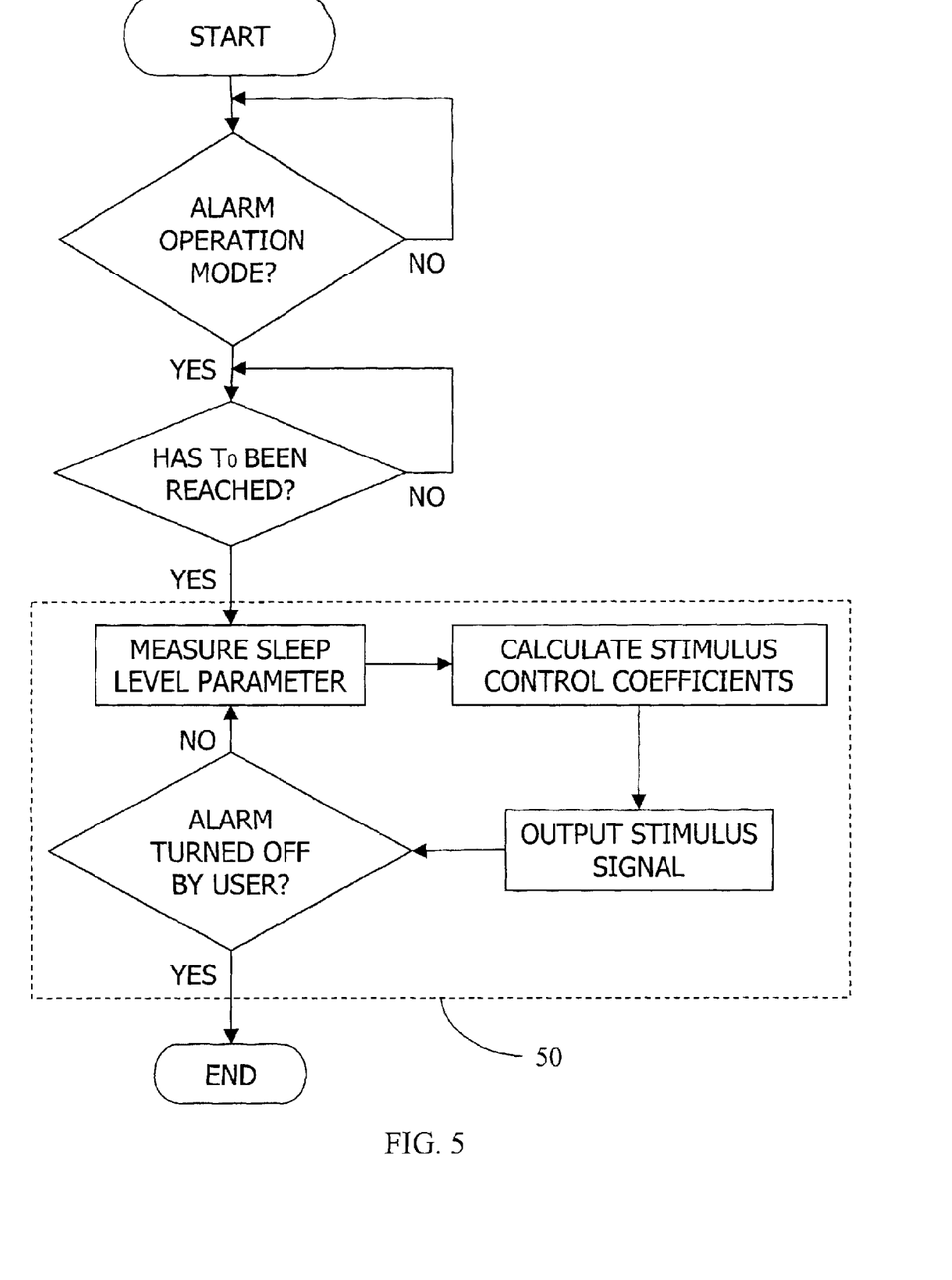
FIG. 5 is a flow chart describing the operation of the waking control system of the waking device.
Figure 6:
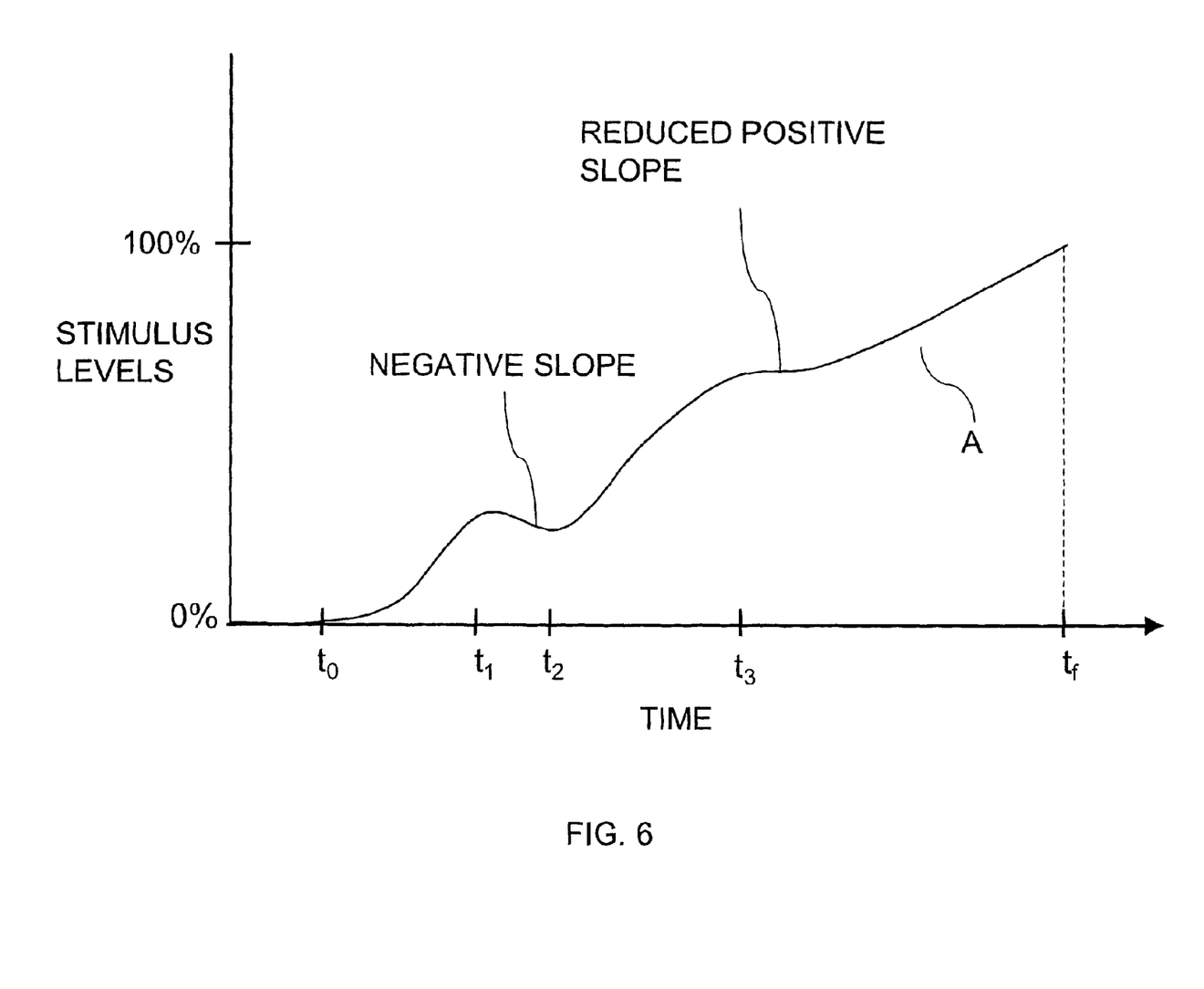
FIG. 6 is a graphical depiction of a user's sleep profile between the stimulus introduction time and the final wakeup time.

Referring to FIGS. 5 and 6, the system operation will be described. FIG. 5 depicts a simplified flow chart algorithm of the controller 12 during normal operation. At the beginning of operation, the controller 12 waits in an idle state until the user sets the alarm operation mode to be "on". Once the alarm is on, the system checks if the actual time has reached the predefined stimulus introduction time $t_o$ (which may be programmed by the user or set automatically by the system). Once this time is reached, the biofeedback detection subsystem 13 begins continually detecting the amplitude and frequency of user motion, and storing the data collected in a memory device (not shown) that is coupled to the microcontroller 12. The frequency of user motion may be determined by recording the time at which a movement exceeding a particular predefined amplitude occurs, and then dividing the number of such events by a unit time interval. When the actual time reaches the stimulus introduction time $t_o$ (which may be programmed by the user or set automatically by the system), the controller 12 begins to introduce stimulus while continuing to monitor other parameters. The intensity of the introduced stimulus depends on the stimulus control coefficients, which the controller 12 continually calculates and updates on the basis of the detected amplitude and frequency of user movement and the actual time relative to the desired final wakeup time. A number of other variables, such as ambient noise level which may or may not be time-dependent, may be included in the calculations by the controller 12. A feedback loop may be used to provide information to the controller 12. As will be explained further below, other personal factors may also contribute to the calculation of the control coefficients. When the time reaches the desired final wakeup time $t_f$, the stimulus intensity will have reached the 100% intensity level, which may be programmed by the user or set automatically by the system. After the user wakes and turns off the alarm, the system is reset until the alarm is set again the next time. The main looping algorithm 50 is repeated at a high frequency sufficient to provide real time control.

As mentioned above, in the preferred embodiment the principal factors influencing the calculation of the stimulus control coefficients are the amplitude and the frequency of the user movements as detected by the biofeedback detection system 13 and the actual time in comparison to the desired final wakeup time $t_f$. When the user is exhibiting high amplitude or high frequency movement at a time prior to the desired wakeup time, the stimulus intensity must be decreased to allow the user to continue sleeping. Conversely, when there is little or no movement, the stimulus level can safely be increased so as to bring the user gradually out of deep slumber towards the waking state. As the actual time nears the desired final wakeup time $t_f$, the stimulus level increases in order to reach the 100% intensity level in a gradual manner by the desired final wakeup time $t_f$. In some embodiments, other personal factors can be incorporated to influence the calculation of the stimulus control coefficients. These optional personal factors can be configured by the user or, in some circumstances, determined by the system. These optional personal control factors include:

(a) personal sensitivity actor: a user may set a personal sensitivity factor on a predetermined scale as to whether the user is a heavy sleeper or a light sleeper. If the personal sensitivity factor indicates that the user is a heavy sleeper, then this would tend to increase the stimulus intensity;

(b) recent sleep history: this parameter could be set by the user or determined by the system based on past system settings (i.e. alarm setting and waking times for the last number of evenings). For example, if the recent sleep history indicates that the user is operating with a sleep deficit, then this would tend to increase the stimulus intensity level;

(c) current night sleep duration: depending on what time the waking device was configured by the user, the system could determine the amount of sleep that the user was going to get in the current night. If the current night sleep duration was relatively short, then this would tend to increase the stimulus intensity;

(d) ambient noise factor: the ambient noise level could be configured on a predetermined scale by the user or determined by the system (i.e. through its voice activation microphone). If the ambient noise level is high, then this would tend to increase the stimulus intensity level; and (e) daylight factor: this factor could be configured by the user or determined by the system from its knowledge of the date. For example, when there is less sunlight in each day (i.e. during the winter), it may be harder to wake the user and this would tend to increase the stimulus intensity.

FIG. 6 is a graph displaying aggregate stimulus level versus time. Notably each stimulus may be independently controlled. Aggregate stimulus represents all independent stimuli considered together. The stimulus introduction time is indicated by the symbol $t_o$ and the final wakeup time is indicated by the symbol $t_f$. The curve A represents the sleep profile of a typical user on a typical day. It should be noted that the sleep profile of each user will vary on any given day and curve A is merely a illustrative example. As can be seen from the curve A, the controller 12 introduces a small amount of stimulus at the stimulus introduction time $t_o$. The amount of stimulus introduced at the stimulus introduction time $t_o$ is typically relatively low, because the user will most likely have been sleeping soundly and so the measured amplitude and frequency of movement will be correspondingly low. The stimulus intensity increases in the region between $t_o$ and $t_1$, but the system detects some degree of user movement around time $t_1$, which causes the slope of the curve A to decrease slightly.

A relatively large amount of movement is detected in the region between $t_1$ and $t_2$, which causes the slope of the curve A to actually become negative. That is, there is a reduction in aggregate stimulus intensity in the region between $t_1$ and $t_o$, to avoid waking the user too early before $t_f$ thereby reducing the amount of sleep time. By $t_2$, the movement has subsided and the stimulus intensity starts to increase again, until further movement is detected around time $t_3$. Once again, the slope of curve A decreases in the region around $t_3$, but the aggregate stimulus level continues to increase. In the region between $t_3$ and $t_f$, the actual time is nearing the final wakeup time $t_f$ and so the remaining time factor begins to dominate the calculation of the stimulus control coefficients, causing the aggregate stimulus level to rise. At the desired final wakeup time $t_f$, the stimulus level has reached 100% of the level preset by the user (or set automatically by the system) and the user is aroused. In this manner, the waking system minimizes the shock to the user's physiology as the individual crosses their personal continuum between being asleep and being awake.

It should be understood that the above description is intended for illustrative purposes only, and is not intended to limit the scope of the present invention in any way. Those skilled in the art will appreciate that various modifications can be made to the embodiments discussed above without departing from the spirit of the present invention.

What is claimed is:

1. An apparatus for waking an individual in a manner that promotes said individual's well being comprising:
   at least one sensor operative to sense at least one parameter correlated to said individual's sleep level; and
   a controller capable of being set by said individual with a final wakeup time, said controller connected to receive sensed values of the at least one parameter from the sensor and configured to introduce a stimulus at a stimulus introduction time prior to the final wakeup time and, over a period between the stimulus introduction time and the final wakeup time, to adjust an intensity of the stimulus based on feedback which comprises the sensed values of the at least one parameter and based on a difference between a current time and the final wakeup time, so as to bring said individual gradually out of sleep and to an awake state over a period of time between the stimulus introduction time and the final wakeup time.

2. An apparatus according to claim 1, wherein said at least one sensor comprises at least one of: an ultrasonic motion detector and an infrared motion detector.

3. An apparatus according to claim 1, wherein said controller is configured to independently adjust an intensity of a plurality of stimuli based on feedback which comprises the sensed values of the at least one parameter and based on a difference between a current time and the final wakeup time.

4. An apparatus according to claim 1, wherein the at least one parameter sensed by said sensor comprises at least one of: motion, brain waves, skin potential, skin resistance, muscle tone, eye movement, heart rate and breathing rate of said individual.

5. An apparatus according to claim 1 comprising a user interface having an input mechanism operative to receive input from said individual and an output mechanism operative to communicate information to said individual.

6. An apparatus according to claim 5, wherein said input mechanism comprises at least one of: a voice recognition system, a keypad, a touch screen interface, a remote control device and a plurality of buttons and switches.

7. An apparatus according to claim 5, wherein said output mechanism comprises at least one of: a liquid crystal display, a light emitting diode display, an analog clock display, a plasma screen display, a cathode ray tube display, an audio output device and a plurality of switch and button indicators.

8. An apparatus according to claim 5, wherein said input mechanism is operative to receive input information from said individual, the input information comprising at least one of: a particular set of stimuli desired, a desired relative intensity of each stimulus selected, the stimulus introduction time, a personal sleep sensitivity level of said individual, a recent sleep history of said individual, an ambient stimulus level in said individual's sleeping environment and a seasonal amount of daylight.

9. An apparatus according to claim 5, wherein said output mechanism is operative to communicate information to said individual, the information comprising at least one of: a particular set of stimuli desired, a relative intensity of each stimulus selected, the stimulus introduction time, a personal sleep sensitivity level of said individual, a recent sleep history of said individual, an ambient stimulus level in said individual's sleeping environment and a seasonal amount of daylight.

10. An apparatus according to claim 1, wherein the stimulus comprises at least one of: a heat stimulus, a light stimulus, a sound stimulus, an olfactory stimulus and a tactile stimulus.

11. An apparatus according to claim 1 wherein the at least one parameter comprises motion of the individual and wherein the controller is configured to adjust the intensity of the stimulus based on both amplitude and frequency of the motion of the individual.

12. An apparatus according to claim 1 wherein the controller is configured to periodically adjust the intensity of the stimulus throughout the period between the stimulus introduction time and the final wakeup time based on the feedback and based on the difference between the current time and the final wakeup time.

13. An apparatus according to claim 1 wherein the controller is configured to periodically adjust the intensity of the stimulus at least three times in the period between the stimulus introduction time and the final wakeup time based on the feedback and based on the difference between the current time and the final wakeup time.

14. An apparatus according to claim 1 wherein the controller is configured to control a rate of change of intensity of the stimulus over time throughout the period between the stimulus introduction time and the final wakeup time based on the feedback and based on the difference between the current time and the final wakeup time.

15. An apparatus according to claim 14 wherein the controller is configured to control the rate of change of intensity of the stimulus over time to be negative if the sensed values of the at least one parameter indicate that the user may reach the awake state prior to the final wakeup time.

16. An apparatus for waking an individual in a manner that promotes said individuals well being comprising:
   a detection system operative to sense at least one parameter correlated to said individuals sleep level; and
   a controller capable of being set by said individual with a final wakeup time, said controller connected to receive sensed values of the at least one parameter from the sensor and configured to introduce at least one stimulus at a stimulus introduction time prior to the final wakeup time and to adjust an intensity of the stimulus over a period of time between the stimulus introduction and the final wakeup time based on feedback which comprises sensed values of the at least one parameter and based on a difference between a current time and the final wakeup time, so as to bring said individual gradually out of sleep and to an awake state over said period of time.

17. An apparatus according to claim 16 wherein the controller is configured to adjust the intensity of the stimulus such that the individual reaches the awake state at about the final wakeup time.

18. An apparatus according to claim 16, wherein the at least one parameter comprises motion of the individual and wherein the controller is configured to adjust the intensity of the stimulus based on both amplitude and frequency of the motion of the individual.

19. An apparatus according to claim 16 wherein the controller is configured to periodically adjust the intensity of the stimulus throughout the period between the stimulus introduction time and the final wakeup time based on the feedback and based on the difference between the current time and the final wakeup time.

20. An apparatus according to claim 16 wherein the controller is configured to periodically adjust the intensity of the stimulus at least three times in the period between the stimulus introduction time and the final wakeup time based on the feedback and based on the difference between the current time and the final wakeup time.

21. An apparatus according to claim 16 wherein the controller is configured to control a rate of change of intensity of the stimulus over time throughout the period between the stimulus introduction time and the final wakeup time based on the feedback and based on the difference between the current time and the final wakeup time.

22. An apparatus according to claim 21 wherein the controller is configured to control the rate of change of intensity of the stimulus over time to be negative if the sensed values of the at least one parameter indicate that the user may reach the awake state prior to the final wakeup time.

23. A method of waking an individual in a manner that promotes said individual's well being, said method comprising:
setting a desired final wakeup time;
sensing at least one parameter correlated to said individual's sleep level;
introducing at least one stimulus to said individual's sleeping environment at a stimulus introduction time prior to said final wakeup time;
over a period between the stimulus introduction time and the final wakeup time, adjusting an intensity of the stimulus based on feedback which comprises sensed values of the at least one parameter and based on a difference between a current time and a final wakeup time, so as to bring said individual gradually out of sleep and to an awake state over a period of time between the stimulus introduction time and the final wakeup time.

24. A method according to claim 23, wherein sensing at least one parameter correlated to said individuals sleep level comprises detecting motion of the individual.

25. A method according to claim 23, comprising independently controlling a plurality of stimuli based on feedback which comprises sensed values of the at least one parameter and based on a difference between a current time and the final wakeup time.

26. A method according to claim 23, wherein sensing at least one parameter correlated to said individual's sleep level comprises sensing at least one of: motion, brain waves, skin potential, skin resistance, muscle tone, eye movement, heart rate and breathing rate of said individual.

27. A method according to claim 23, comprising receiving input information from said individual, said input information comprising at least one of: a particular set of stimuli desired, a desired relative intensity of each stimulus selected, the stimulus introduction time, a personal sleep sensitivity level of said individual, a recent sleep history of said individual, an ambient stimulus level in said individuals sleeping environment and a seasonal amount of daylight.

28. A method according to claim 23, comprising communicating output information to said individual, said output information comprising at least one of: a particular set of stimuli desired, a relative intensity of each stimulus selected, the stimulus introduction time, a personal sleep sensitivity level of said individual, a recent sleep history of said individual, an ambient stimulus level in said individual's sleeping environment and a seasonal amount of daylight.

29. A method according to claim 23, wherein introducing at least one stimulus to said individual's sleeping environment comprises introducing at least one of: a heat stimulus, a light stimulus, a sound stimulus, an olfactory stimulus and a tactile stimulus.

30. A method according to claim 23, wherein sensing at least one parameter correlated to said individuals sleep level comprises detecting motion of the individual and wherein adjusting the intensity of the stimulus comprises adjusting the intensity of the stimulus based on both amplitude and frequency of the motion of the individual.

31. A method according to claim 23 wherein adjusting the intensity of the stimulus comprises periodically adjusting the intensity of the stimulus throughout the period between the stimulus introduction time and the final wakeup time based on the feedback and based on the difference between the current time and the final wakeup time.

32. A method according to claim 23 wherein adjusting the intensity of the stimulus comprises periodically adjusting the intensity of the stimulus at least three times in the period between the stimulus introduction time and the final wakeup time based on the feedback and based on the difference between the current time and the final wakeup time.

33. A method according to claim 23 comprising controlling a rate of change of intensity of the stimulus over time throughout the period between the stimulus introduction time and the final wakeup time based on the feedback and based on the difference between the current time and the final wakeup time.

34. A method according to claim 33, comprising controlling the rate of change of intensity of the stimulus over time to be negative if the sensed values of the at least one parameter indicate that the user may reach the awake state prior to the final wakeup time.

35. A method of waking an individual in a manner that promotes said individual's well being, said method comprising:
setting a desired final wakeup time;
measuring at least one parameter correlated to said individuals sleep level;
introducing at least one stimulus to said individual's sleeping environment at a stimulus introduction time prior to said final wakeup time; and
adjusting an intensity of the stimulus over a period of time between the stimulus introduction time and the final wakeup time based on feedback which comprises sensed values of the at least one parameter sensed during the period of time and based on a difference between a current time and the final wakeup time, so as to bring said individual gradually out of sleep and to an awake state over said period of time.

36. A method according to claim 35 wherein adjusting the intensity of the stimulus comprises adjusting the intensity of the stimulus such that said individual reaches the awake state at about the final wakeup time.

37. A method according to claim 35 wherein sensing at least one parameter correlated to said individuals sleep level comprises detecting motion of the individual and wherein adjusting the intensity of the stimulus comprises adjusting the intensity of the stimulus based on both amplitude and frequency of the motion of the individual.

38. A method according to claim 35, wherein adjusting the intensity of the stimulus comprises periodically adjusting the intensity of the stimulus throughout the period between the stimulus introduction time and the final wakeup time based on the feedback and based on the difference between the current time and the final wakeup time.

39. A method according to claim 35, wherein adjusting the intensity of the stimulus comprises periodically adjusting the intensity of the stimulus at least three times in the period between the stimulus introduction time and the final wakeup time based on the feedback and based on the difference between the current time and the final wakeup time.

40. A method according to claim 35, comprising controlling a rate of change of intensity of the stimulus over time throughout the period between the stimulus introduction time and the final wakeup time based on the feedback and based on the difference between the current time and the final wakeup time.

41. A method according to claim 40 comprising controlling the rate of change of intensity of the stimulus over time to be negative if the sensed values of the at least one parameter indicate that the user may reach the awake state prior to the final wakeup time.

* * * * *